United States Patent
Snyder

(10) Patent No.: US 10,959,931 B2
(45) Date of Patent: Mar. 30, 2021

(54) TABLET INCLUDING ABRASIVE FOR DENTAL CLEANING

(71) Applicant: WATER PIK, INC., Fort Collins, CO (US)

(72) Inventor: Clifford Snyder, Fort Collins, CO (US)

(73) Assignee: WATER PIK, INC., Fort Collins, CO (US)

( * ) Notice: Subject to any disclaimer, the term of this patent is extended or adjusted under 35 U.S.C. 154(b) by 0 days.

(21) Appl. No.: 15/887,626

(22) Filed: Feb. 2, 2018

(65) Prior Publication Data

US 2018/0221260 A1 Aug. 9, 2018

Related U.S. Application Data

(60) Provisional application No. 62/453,949, filed on Feb. 2, 2017.

(51) Int. Cl.

| | |
|---|---|
| A61K 8/44 | (2006.01) |
| A61K 8/02 | (2006.01) |
| A61K 8/34 | (2006.01) |
| A61K 8/25 | (2006.01) |
| A61K 8/36 | (2006.01) |
| A61K 8/46 | (2006.01) |
| A61K 8/60 | (2006.01) |
| A61Q 11/00 | (2006.01) |
| A61K 8/81 | (2006.01) |
| C09K 3/14 | (2006.01) |

(52) U.S. Cl.
CPC ............ *A61K 8/445* (2013.01); *A61K 8/0216* (2013.01); *A61K 8/0241* (2013.01); *A61K 8/25* (2013.01); *A61K 8/345* (2013.01); *A61K 8/361* (2013.01); *A61K 8/44* (2013.01); *A61K 8/463* (2013.01); *A61K 8/60* (2013.01); *A61K 8/8176* (2013.01); *A61Q 11/00* (2013.01); *C09K 3/14* (2013.01); *A61K 2800/28* (2013.01); *A61K 2800/92* (2013.01)

(58) Field of Classification Search
CPC .......... A61C 17/02; A61K 8/02; A61K 31/19; A61K 33/06
USPC ....................................................... 424/682
See application file for complete search history.

(56) References Cited

U.S. PATENT DOCUMENTS

| | | | |
|---|---|---|---|
| 3,932,605 A | 1/1976 | Vit | |
| 4,174,571 A | 11/1979 | Gallant | |
| 4,308,252 A | 12/1981 | Tomaich et al. | |
| 5,506,248 A | 4/1996 | Nikfar et al. | |
| 6,024,987 A * | 2/2000 | Jettka | A61K 9/0056 424/682 |
| 6,245,732 B1 | 6/2001 | Gallon et al. | |
| 6,329,334 B1 | 12/2001 | Bertleff et al. | |
| 6,605,583 B1 | 8/2003 | Gorlin | |
| 6,607,711 B2 | 8/2003 | Pedersen et al. | |
| 6,648,644 B1 | 11/2003 | Flemmig et al. | |
| 7,083,411 B2 | 8/2006 | Flemmig et al. | |
| 8,652,495 B2 | 2/2014 | Porter et al. | |
| 8,858,921 B2 | 10/2014 | Schmid et al. | |
| 9,358,185 B2 | 6/2016 | Haeberlein et al. | |
| 9,493,731 B2 | 11/2016 | Mueller | |
| 9,498,416 B2 | 11/2016 | Li et al. | |
| 9,532,932 B2 | 1/2017 | Prencipe et al. | |
| 2002/0122823 A1 | 9/2002 | Bunick et al. | |
| 2004/0091429 A1 | 5/2004 | Flemmig et al. | |
| 2004/0101493 A1 | 5/2004 | Scott et al. | |
| 2005/0214388 A1 | 9/2005 | Gorham et al. | |
| 2006/0159759 A1* | 7/2006 | Ohta | A61K 9/0058 424/472 |
| 2006/0160046 A1 | 7/2006 | Nesbitt et al. | |
| 2006/0222600 A1 | 10/2006 | Pinyayev | |
| 2008/0170991 A1 | 7/2008 | Shi et al. | |
| 2008/0255498 A1 | 10/2008 | Houle | |
| 2008/0312168 A1 | 12/2008 | Pilgaonkar et al. | |
| 2009/0186081 A1 | 7/2009 | Holm et al. | |
| 2010/0330013 A1 | 12/2010 | O'Connell et al. | |
| 2011/0027328 A1 | 2/2011 | Baig et al. | |
| 2012/0141953 A1* | 6/2012 | Mueller | A61C 3/025 433/88 |
| 2013/0337413 A1 | 12/2013 | Donnet et al. | |
| 2015/0125814 A1 | 5/2015 | Haeberlein et al. | |
| 2015/0232511 A1 | 8/2015 | Hug et al. | |
| 2016/0100921 A1* | 4/2016 | Ungar | A61C 17/02 433/89 |
| 2016/0220452 A1 | 8/2016 | Donnet | |

(Continued)

FOREIGN PATENT DOCUMENTS

| | | |
|---|---|---|
| AT | 337645 B | 7/1977 |
| AU | 604721 B2 | 1/1991 |

(Continued)

OTHER PUBLICATIONS

Graumann et al., "Air Polishing: A Review of Current Literature." The Journal of Dental Hygiene (2013) vol. 87, No. 4, pp. 173-180 (Year: 2013).*

Tousey, Michael D., "The Granulation Process 101: Basic Technologies for Tablet Making." Pharmaceutical Technology Tableting & Granulation 2002; pp. 8-13. (Year: 2002).*

International Search Report and Written Opinion mailed in International application PCT/IB2011/001327 dated Nov. 17, 2011, 10 pages.

International Search Report and Written Opinion dated Sep. 12, 2018, in PCT Application No. PCT/US/2018/016505, 13 pages.

*Primary Examiner* — Walter E Webb
(74) *Attorney, Agent, or Firm* — Dorsey & Whitney LLP

(57) ABSTRACT

Consumable abrasive-containing oral hygiene tablets are described. The tablets include glycine as an abrasive. The glycine average (Mv) particle size may be greater than 45 μm. The tablets may be used with an oral irrigator and, when placed in the irrigator's fluid flow path, may disintegrate, release the abrasive, and improve the cleaning efficacy of the irrigator.

21 Claims, 2 Drawing Sheets

(56) References Cited

U.S. PATENT DOCUMENTS

| | | |
|---|---|---|
| 2017/0027848 A1 | 2/2017 | Li |
| 2017/0087065 A1 | 3/2017 | Berglund et al. |

FOREIGN PATENT DOCUMENTS

| | | |
|---|---|---|
| CH | 695191 A5 | 1/2006 |
| DE | 29723656 U1 | 11/1998 |
| DE | 19847283 A1 | 4/2000 |
| DE | 19922578 A1 | 11/2000 |
| DE | 19934704 A1 | 1/2001 |
| DE | 10130762 A1 | 1/2003 |
| DE | 60101482 T2 | 1/2004 |
| DE | 69730599 T2 | 10/2004 |
| DE | 10330762 A1 | 2/2005 |
| DE | 60019084 T2 | 5/2005 |
| DE | 10123621 B4 | 12/2006 |
| DE | 69637030 T2 | 5/2007 |
| DE | 102006021401 A1 | 12/2007 |
| DE | 602005002917 T2 | 2/2008 |
| DE | 69839342 T2 | 5/2008 |
| EP | 0002293 A1 | 6/1979 |
| EP | 0522766 A2 | 1/1993 |
| EP | 0628627 A1 | 12/1994 |
| EP | 0673644 A1 | 9/1995 |
| EP | 0716144 A2 | 6/1996 |
| EP | 0812808 A1 | 12/1997 |
| EP | 0846756 A1 | 6/1998 |
| EP | 0957159 A1 | 11/1999 |
| EP | 1048719 A1 | 11/2000 |
| EP | 1202663 B1 | 2/2003 |
| EP | 1371719 A1 | 12/2003 |
| EP | 1375636 A1 | 1/2004 |
| EP | 1382668 A1 | 1/2004 |
| EP | 1405900 A1 | 4/2004 |
| EP | 1405901 A1 | 4/2004 |
| EP | 1405902 A1 | 4/2004 |
| EP | 1418224 A1 | 5/2004 |
| EP | 1144585 B1 | 3/2005 |
| EP | 1533427 A1 | 5/2005 |
| EP | 1669438 B1 | 10/2007 |
| EP | 1919435 B1 | 7/2011 |
| EP | 2515784 A1 | 10/2012 |
| EP | 2753292 A2 | 7/2014 |
| ES | 2292051 T3 | 3/2008 |
| GB | 848235 A | 9/1960 |
| GB | 989683 A | 4/1965 |
| GB | 1423536 A | 2/1976 |
| WO | 9313658 A1 | 7/1993 |
| WO | 9518215 A1 | 7/1995 |
| WO | 9800467 A1 | 1/1998 |
| WO | 9831298 A1 | 7/1998 |
| WO | 9854284 A1 | 12/1998 |
| WO | 9940171 A1 | 8/1999 |
| WO | 0017311 A1 | 3/2000 |
| WO | 0058435 A1 | 10/2000 |
| WO | 0198448 A1 | 12/2001 |
| WO | 03104380 A1 | 12/2003 |
| WO | 2010077468 A1 | 7/2010 |
| WO | 2013072932 A2 | 5/2013 |
| WO | 2013080762 A1 | 6/2013 |
| WO | 2016052572 A1 | 4/2016 |
| WO | 2016062742 A1 | 4/2016 |
| WO | 2016124381 A1 | 8/2016 |
| WO | 2018144771 A2 | 8/2018 |

\* cited by examiner

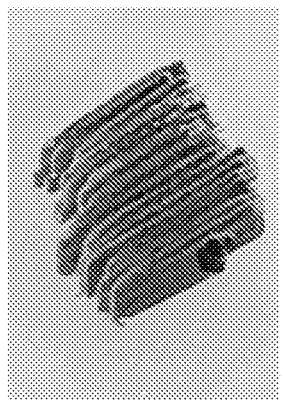
FIG. 2A
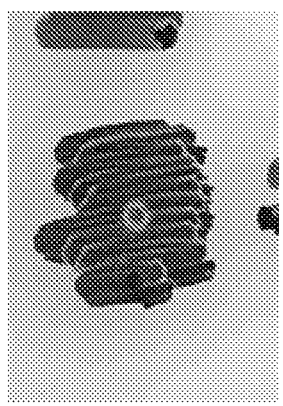
Fig. 2B
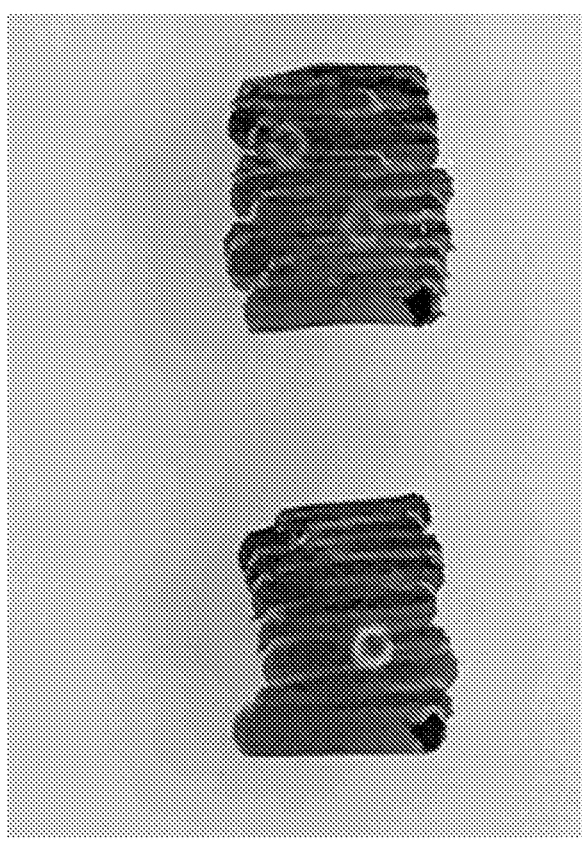
Fig. 2D
Fig. 2C

TABLET INCLUDING ABRASIVE FOR DENTAL CLEANING

CROSS-REFERENCE TO RELATED APPLICATIONS

This application claims priority to U.S. Provisional Patent Application No. 62/453,949, filed Feb. 2, 2017, the contents of which are hereby incorporated by reference in their entirety.

TECHNICAL FIELD

The present disclosure relates to oral hygiene tablets comprising an abrasive, and methods of making and using the same.

BACKGROUND

Human tooth decay is the damage caused by acid erosion of a tooth. Bacteria in the mouth produce the eroding acids when they eat sugars in foods people eat. Over time, the acids destroy enamel, the outer layer of a tooth, and even dentin, the middle layer. Decay can be formed as a hole or cavity.

Teeth can be extrinsically stained by foods such as berries and chocolate, drinks such as coffee, wine, and dark-colored sodas, and smoking. Extrinsic stains range from white streaks to yellow tints or brown spots and pits.

Some tooth decay and stains can be removed by a dental professional with air abrasion, a technique in which fine abrasive particles are propelled toward the tooth surface by compressed air or gas running through a dental handpiece. Small areas of decay or stain are removed as the stream of abrasive particles strike affected regions.

Air abrasion can be uncomfortable for a patient and harsh on teeth because the procedure removes small portions of the tooth surface. Air abrasion is also messy, as the procedure produces a cloud of fine dust. The fine particles can expose the patient and dental professionals to inhalation-associated health risks.

Powder jet devices, which combine an air-abrasive mixture with water and spray the composition onto teeth, may present health risks from inhalation of fine particles. The abrasive particles also remove small areas of the tooth surface.

Stains can be reduced or removed by bleaching the teeth. Dental professionals can apply a light-activated bleaching gel held against the teeth in trays for about 30 to 60 minutes. Home bleaching trays use a weaker bleaching agent. Consistent home bleaching practice can reduce stains over the course of several weeks or months. Less harsh, but also less effective, home remedies include whitening gels and strips applied to the teeth. Regular brushing of the teeth can also help prevent or reduce stains, but can also be harsh on the teeth.

The information included in this Background section of the specification, including any references cited herein and any description or discussion thereof, is included for technical reference purposes only and is not to be regarded as subject matter by which the scope of the invention as defined in the claims is to be bound.

SUMMARY

The technology disclosed herein relates to oral hygiene tablets. The tablets may be used to reduce or remove stains or decay from tooth enamel or dentin or clean root surfaces while causing no or minimal abrasion of the teeth surfaces.

In some embodiments, the tablets include one or more of an abrasive, a bulking agent, a glidant, a binder, a disintegrant, a lubricant, a surfactant, a sweetener, and a flavoring agent. In some embodiments, the abrasive is an amino acid. In some embodiments, the amino acid is glycine. In some embodiments, the bulking agent is xylitol. In some embodiments, the glidant is silica.

In some embodiments, the glycine has an average particle size of greater than 45 µm as measured by volume distribution. In some embodiments, 35% by weight or less of the glycine particles have a particle size below 45 µm. In some embodiments, 35% by weight or less of the glycine particles have a particle size greater than 100 µm.

In some embodiments, the glycine is present in the tablets at 32 wt % to 48 wt %. In some embodiments, the xylitol is present in the tablets at 32 wt % to 48 wt %.

In some embodiments, the silica is fumed silica. The average particle size of the fumed silica may be greater than 0.03 µm. In some embodiments, the silica is present in the tablets at 0.28 wt % to 0.42 wt %.

In some embodiments, the tablet includes a lubricant and the lubricant is magnesium stearate. In some embodiments, the tablet includes a surfactant and the surfactant is sodium lauryl sulfate. In some embodiments, the tablet includes a sweetener and the sweetener is sucralose.

In one implementation, a method for making the tablets is provided. The tablets may be formed by granulation and compression.

In one implementation, a method for using the tablets, such as to reduce stain on a tooth, is provided. The method may include providing a tablet containing an abrasive and eroding the tablet with a fluid stream to produce a suspension of particles in the fluid. The particles may be transported to the tooth by the fluid stream.

In some implementations, the glycine abrades the stain from the tooth.

In some implementations, the stain shows an average 27% improvement in a modified Lobene Stain Index after 2 minutes of application of the particle-laden fluid. In some implementations, the stain shows an average 64% improvement in a modified Lobene Stain Index after 5 minutes of application of the particle-laden fluid.

In some implementations, less dentin is abraded by the method than by brushing with a toothbrush for 10 times the amount of time In some implementations, less than 0.2 µm of dentin is abraded after 48 seconds of application of the particle-laden fluid.

In some embodiments, an abrasive, such as glycine, is entrained in a stream of fluid, such as water. In some embodiments, the stream is pulsating. In some embodiments, the stream pulsates at about 1200 pulses per minute.

In some embodiments, the pulsating action is produced by a pump, such as a piston pump. In some embodiments, the pulsating action is produced when pressurized fluid flows through a valve, such as an intermittent valve or an oscillating valve.

In some embodiments, the stream is ejected from an oral irrigator, a countertop-mounted irrigation device, a handheld irrigation device, or a water line.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIGS. 2A-2D illustrate the effects of various treatments on tooth stain removal.

DETAILED DESCRIPTION

Figure 1:
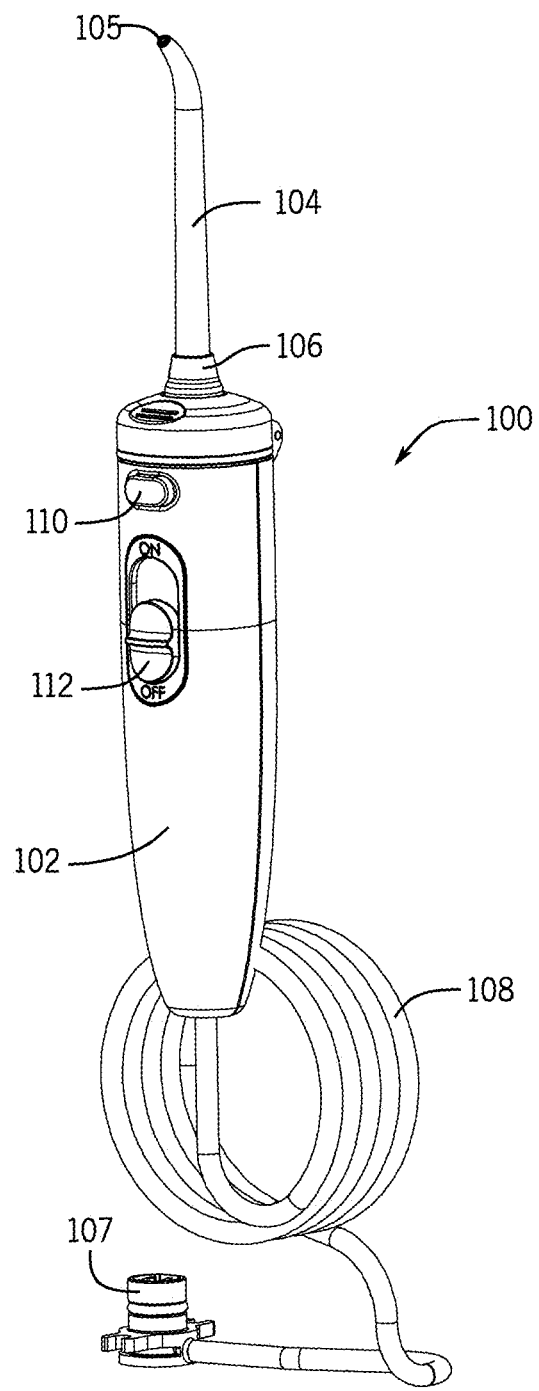
FIG. 1 is a front right isometric view of a handle for an oral irrigator connected to a hose connectable to a base unit.

Oral hygiene tablets for cleaning teeth are disclosed herein. The tablets may reduce or remove stains or decay from tooth enamel or dentin or clean root surfaces. The tablets may be generally understood as containing an abrasive capable of cleaning teeth while causing no or minimal abrasion of the teeth surfaces. The abrasive may be glycine and the tablets may include excipients such as a bulking agent and glidant.

Abrasive Tablet Formulations

Tablet formulations may be generally understood as including an abrasive and a plurality of excipients. Excipients may include bulking agents, binders, disintegrants, glidants, lubricant, surfactants, sweeteners, flavoring agents, and water. Any given excipient may act as more than one type of excipient or may serve more than one function. For example, a bulking agent may also be a binder. As another example, a sweetener may also be a flavoring agent.

The abrasive may be any material capable of polishing or cleaning a natural or artificial tooth surface. Examples of abrasives include aluminum hydroxide, aluminum oxide, boron, calcium carbonate, calcium sodium phosphosilicate, emery, garnet, glycine, perlite, pumice, silicon carbide, sodium bicarbonate, zirconium oxide, and zirconium silicate.

In one embodiment, the abrasive is an amino acid. In one embodiment, the abrasive is glycine. The glycine may have an MV (mean diameter of the volume distribution) particle size of greater than 45 µm, or about 50 µm to about 100 µm, or about 50 µm to about 90 µm, or about 50 µm to about 80 µm, or about 70 µm to about 100 µm, or about 50 µm to about 60 µm. In some embodiments, the glycine particle size (MV) is about 58 µm to about 60 m. In one embodiment, the glycine particle size is about 59 µm.

In some embodiments, about 35 weight percent or less of the glycine particles have a particle size below 45 µm. In some embodiment, about 35 weight percent or less of the glycine particles have a particle size greater than 100 µm.

The size distribution of the glycine particles may be about 1 µm to about 500 µm, or about 1 µm to about 400 µm, or about 1 µm to about 300 µm, or about 2 µm to about 300 µm.

The glycine particles may not include a surface coating.

The abrasive may be present at about 20 weight percent to about 60 weight percent of a tablet, or about 20 weight percent to about 55 weight percent, or about 20 weight percent to about 50 weight percent, or about 20 weight percent to about 45 weight percent, or about 20 weight percent to about 40 weight percent, or about 25 weight percent to about 60 weight percent, or about 30 weight percent to about 60 weight percent, or about 35 weight percent to about 40 weight percent, or about 32 weight percent to about 48 weight percent of the tablet. In one embodiment, the abrasive is present at about 40 weight percent of the tablet.

Glycine is a water soluble amino acid having a Mohs hardness value of 2. Abrasives used in dental air polishing include sodium bicarbonate (Mohs hardness value of 2.5), calcium carbonate (Mohs hardness value of 3), and aluminum hydroxide (Mohs hardness value of 4). In the design and use of an oral hygiene tablet, glycine, which has a Mohs hardness value less than that of either enamel (5.0) or dentin (3.0-4.0), may yield a safer or gentler abrasive than known abrasives with higher hardness values. In the design and use of an oral hygiene tablet, glycine, which is a regularly consumed amino acid, may be safe and non-toxic in case of ingestion.

The bulking agent or filler may be any material that adds volume or weight, which may aid in processing or manufacturing and may make a tablet size more practical for a subject. Examples of bulking agents include starch, maltodextrin, calcium salts, and sugars such as lactose.

In one embodiment, the bulking agent is xylitol. In one embodiment, the bulking agent is xylitol co-processed with maize dextrin, such as Xylisorb® 100 DC (Roquette Pharma, Lestrem, France).

The bulking agent may be present at about 20 weight percent to about 60 weight percent of a tablet, or about 20 weight percent to about 55 weight percent, or about 20 weight percent to about 50 weight percent, or about 20 weight percent to about 45 weight percent, or about 20 weight percent to about 40 weight percent, or about 25 weight percent to about 60 weight percent, or about 30 weight percent to about 60 weight percent, or about 35 weight percent to about 40 weight percent, or about 32 weight percent to about 48 weight percent of the tablet. In one embodiment, the bulking agent is present at about 40 weight percent of the tablet.

In the design and use of an oral hygiene tablet, Xylisorb® may help produce harder tablets that dissolve more cleanly. The tablets may dissolve without producing a pasty material. When the tablet is used in the fluid flow path of an oral irrigator, the tablet may dissolve without blocking the flow path or clogging irrigator components such as a screen.

The binder may be any material capable of holding or drawing other materials together to form a cohesive whole. Binders may also help tablets be formed with the required mechanical strength. Examples of binders include disaccharides such as sucrose and lactose; starches such as corn starch; cellulose; modified celluloses such as microcrystalline cellulose, hydroxypropyl cellulose, hydroxypropyl methyl cellulose, and hydroxypropyl ethyl cellulose; sugar alcohols such as xylitol, sorbitol, and maltitol; gelatin; synthetic polymers such as polyvinylpyrrolidone and polyethylene glycol; and dibasic calcium phosphate, In one embodiment, the binder is a vinylpyrrolidone-vinyl acetate copolymer. In one embodiment, the vinylpyrrolidone-vinyl acetate copolymer is Kollidon® VA64 Fine (BASF Corporation, Florham Park, N.J.).

The binder may be present at about 0 weight percent to about 12 weight percent of a tablet, or about 0 weight percent to about 10 weight percent, or about 0 weight percent to about 8 weight percent, or about 0 weight percent to about 6 weight percent, or about 2 weight percent to about 10 weight percent, or about 4 weight percent to about 10 weight percent, or about 6 weight percent to about 10 weight percent of the tablet.

In the design and use of an oral hygiene tablet, Kollidon® VA64 Fine may help produce harder tablets that are less susceptible to capping during tableting that tablets made with other binders. Tablets made with Kollidon® VA64 Fine may also be less brittle.

The disintegrant may be any material that facilitates or hastens dissolution of a tablet. Examples of disintegrants include cellulose derivatives such as low-substituted hydroxypropyl cellulose, carboxymethyl cellulose, calcium carboxymethyl cellulose, and internally crosslinked sodium carboxymethyl cellulose (croscarmellose sodium); cross-linked polyvinylpyrrolidone (crospovidone or copovidone); and chemically modified starches such as carboxymethyl starch, sodium carboxymethyl starch, and sodium starch glycolate.

In one embodiment, the disintegrant is a crospovidone. In one embodiment, the crospovidone is Kollidon® CL-F (BASF Corporation, Florham Park, N.J.).

The disintegrant may be present at about 0 weight percent to about 6 weight percent of a tablet, or about 0 weight percent to about 5 weight percent, or about 0 weight percent to about 4 weight percent, or about 0 weight percent to about 3 weight percent, or about 1 weight percent to about 6 weight percent, or about 2 weight percent to about 6 weight percent, or about 3 weight percent to about 6 weight percent of the tablet.

The glidant may be any material that optimizes the flow of a powder to be tableted. Examples of glidants include colloidal silicon dioxide (fumed silica), starch, and talc.

In one embodiment, the glidant is fumed silica. In some embodiments, the fumed silica is not water repellant. In one embodiment, the non-water repellant fumed silica is Aerosil® 200 (Evonik Industries, Essen, Germany).

The fumed silica may have an average particle size of greater than 0.03 µm, or about 0.06 µm to 0.18 µm, or about 0.06 µm to 0.16 µm, or about 0.06 µm to 0.14 µm, or about 0.06 µm to 0.12 µm, or about 0.08 µm to 0.18 µm, or about 0.10 µm to 0.18 µm, or about 0.12 µm to 0.18 µm. In one embodiment, the average particle size is about 0.12 µm.

The glidant may be present at about 0 weight percent to about 0.6 weight percent of a tablet, or about 0 weight percent to about 0.5 weight percent, or about 0 weight percent to about 0.4 weight percent, or about 0 weight percent to about 0.3 weight percent, or about 0.1 weight percent to about 0.6 weight percent, or about 0.2 weight percent to about 0.6 weight percent, or about 0.3 weight percent to about 0.6 weight percent of the tablet. In one embodiment, the glidant is present at about 0.28 weight percent to about 0.42 weight percent. In one embodiment, the glidant is present at about 0.35 weight percent of the tablet.

In the design and use of an oral hygiene tablet, the relatively small Aerosil® 200 particles may help coat larger component particles, thereby reducing van der Waals attractive forces between them. The fumed silica particles may also help absorb moisture present on the surface of the powders, thereby minimizing powder caking and clumping. The fumed silica particles may help optimize powder flow, increase throughput, and improve dosage uniformity.

The lubricant may be any material that prevents components from clumping together or from sticking to machinery such as tablet punches or capsule filling machines. The lubricant may also help reduce friction and thereby aid in die filling, tablet formation, and ejection.

Examples of lubricants include stearic acid; stearic acid metal salts such as calcium stearate or magnesium stearate; talc; colloidal silica; silicic acids such as silicic anhydride or silicate hydrate; waxes such as beeswax or spermaceti; glycerin fatty acid esters; hydrogenated vegetable oil; boric acid; adipic acid; sulfates such as sodium sulfate; lauryl sulfates such as sodium lauryl sulfate or magnesium lauryl sulfate; glycol; fumaric acid; sodium stearyl fumarate: sodium benzoate; and D,L-leucine. In one embodiment, the lubricant is magnesium stearate.

The lubricant may be present at about 0.5 weight percent to about 2.5 weight percent of a tablet, or about 0.5 weight percent to about 2.25 weight percent, or about 0.5 weight percent to about 2.0 weight percent, or about 0.5 weight percent to about 1.75 weight percent, or about 0.5 weight percent to about 1.5 weight percent, or about 0.75 weight percent to about 2.5 weight percent, or about 1.0 weight percent to about 2.5 weight percent, or about 1.25 weight percent to about 2.5 weight percent, or about 1.5 weight percent to about 2.5 weight percent of the tablet. In one embodiment, the lubricant is present at about 1.5 weight percent of the tablet.

In the design and use of an oral hygiene tablet, the magnesium stearate may help prevent the tablets from sticking to the punch. Magnesium stearate may also help create a barrier to moisture during the tableting process and may help the tablets resist deterioration when touched with wet fingers.

In addition to, or as an alternative to, including a lubricant, the tablet may be coated, such as with a polymeric coating or shellac coating. The coating may be water insoluble and may help the tablets resist deterioration when touched with moist fingers.

The surfactant may be any material that prevents agglomeration, aids flow, improves wetting, promotes deaggregation, increases surface area of particles available for dissolution, and/or increases dissolution rate.

Examples of surfactants include sodium lauryl sulfate, polyethylene glycol, and polysorbate 80. In one embodiment, the surfactant is sodium lauryl sulfate.

The surfactant may be present at about 0.5 weight percent to about 3.0 weight percent of a tablet, or about 0.5 weight percent to about 2.5 weight percent, or about 0.5 weight percent to about 2.25 weight percent, or about 0.5 weight percent to about 2.0 weight percent, or about 0.75 weight percent to about 3.0 weight percent, or about 1.0 weight percent to about 3.0 weight percent, or about 1.25 weight percent to about 3.0 weight percent, or about 1.5 weight percent to about 3.0 weight percent, or about 1.75 weight percent to about 3.0 weight percent, or about 2.0 weight percent to about 3.0 weight percent of the tablet. In one embodiment, the surfactant is present at about 2.0 weight percent of the tablet.

The sweetener may be any material that helps improve the flavor of the tablet or user acceptance of the tablet.

Examples of sweeteners include natural sweeteners such as a dextrose, lactose, mannitol, and sucrose; and artificial sweeteners such as aspartame, cyclamate, saccharin, and sucralose. In one embodiment, the sweetener is sucralose.

The sweetener may be present at about 4 weight percent to about 14 weight percent of a tablet, or about 4 weight percent to about 12 weight percent, or about 4 weight percent to about 10 weight percent, or about 4 weight percent to about 8 weight percent, or about 6 weight percent to about 14 weight percent, or about 8 weight percent to about 14 weight percent, or about 10 weight percent to about 14 weight percent of the tablet. In one embodiment, the sweetener is present at about 9 weight percent of the tablet.

The flavoring agent may be any material that helps mask unpleasant-tasting components and improve user acceptance of the tablet.

Flavoring agents may be natural or artificial. Examples of flavoring agents include sweeteners such as sodium saccharin and aspartame; sour flavorings such as citric acid, malic acid, and tartaric acid; mint flavorings such as peppermint and spearmint; and fragrances such as menthol, lemon, and orange. In one example, the flavoring agent is peppermint spray dried.

The flavoring agent may be present at about 5 weight percent to about 15 weight percent of a tablet, or about 5 weight percent to about 13 weight percent, or about 5 weight percent to about 11 weight percent, or about 5 weight percent to about 9 weight percent, or about 7 weight percent to about 15 weight percent, or about 9 weight percent to about 15 weight percent, or about 11 weight percent to about 15 weight percent of the tablet. In one embodiment, the flavoring agent is present at about 10 weight percent of the tablet.

In some embodiments, the tablet formulations include water. Water may be present at less than about 0 weight percent to about 5 weight percent, about 0 weight percent to about 4 weight percent, about 0 weight percent to about 3 weight percent, about 0 weight percent to about 2 weight percent, or about 0 weight percent to about 1 weight percent of the tablet.

Although reference is made herein to tablets, the disclosed formulation may be prepared as any solid oral dosage form including pills, capsules, and variants thereof such as caplets.

The tablets may be any shape, such as generally cylindrical. In some embodiment, the tablets have opposing ends and one or both of the ends are rounded or pointed. In some embodiments, the tablets are sized and shaped to fit inside a chamber within an oral irrigator or an oral irrigator tip. In some examples, the tablets may have a thickness of about 7 mm to about 15 mm, or about 7 mm to about 14 mm, or about 7 mm to about 13 mm, or about 7 mm to about 12 mm, or about 7 mm to about 11 mm, or about 8 mm to about 15 mm, or about 9 mm to about 15 mm, or about 10 mm to about 15 mm, or about 11 mm to about 15 mm.

In another example, the tablets are about 40 mm to 50 mm wide and about 20 mm to about 30 mm tall (thick). In another example, the tablets are about 80 mm to 120 mm wide and about 80 mm to about 120 mm thick.

The tablets may have a hardness of about 0.5 kiloponds (kp) to about 10 kp, or about 0.5 kp to about 9 kp, or about 0.5 kp to about 8 kp, or about 0.5 kp to about 7 kp, or about 0.5 kp to about 6 kp, or about 1 kp to about 10 kp, or about 2 kp to about 10 kp, or about 3 kp to about 10 kp, or about 4 kp to about 10 kp, or about 5 kp to about 10 kp. In some embodiments, the tablet has a hardness of about 6 kp to about 8 kp, or about 7 kp.

Methods of Making Tablets

The presently disclosed tablets may be produced by granulation of the components and then forming the mixture into tablets. Granulation may be wet granulation or dry granulation. All components may be mixed together at once or some components, such as the abrasive, bulking agent, and binder may be granulated together first before mixing in other components, such as a lubricant. In some embodiments, the granulated components are dried and screened for size before adding additional components. The mixture may then be pressed into a solid dosage form, such as a tablet. The tablets may be compressed such that they withstand packaging, shipping, and storage yet dissolve when impinged by fluid flowing through an oral irrigator.

In one example, tablet components except for the lubricant are mixed dry before addition of the lubricant. The resulting powder may then be placed directly into a tableting press, which may have one or both of a long stroke and a pre-compression station. In some examples, no additional preparatory steps such as wet granulation, slugging, or roller compaction are utilized. In some examples, one or more additional preparatory steps such as wet granulation, slugging, or roller compaction are included, which may help obtain a denser tablet on a press with less stroke or on a press without a pre-compression station.

In some examples, tableting pressure and/or binder weight percentage may be varied in order to vary the hardness of the tablet and thereby vary either or both of the disintegration time and friability of the tablet.

The tableting pressure (compression force) may be from about 250 pounds to about 10,000 pounds, about 250 pounds to about 9000 pounds, or about 250 pounds to about 8000 pounds, or about 250 pounds to about 7000 pounds, or about 250 pounds to about 6000 pounds, or about 500 pounds to about 10,000 pounds, or about 1000 pounds to about 10,000 pounds, or about 2000 pounds to about 10,000 pounds, or about 3000 pounds to about 10,000 pounds, or about 4000 pounds to about 10,000 pounds, or about 5000 pounds to about 10,000 pounds, or about 6000 pounds to about 10,000 pounds, In some embodiments, the pre-compression force is about 1100 pounds to about 3300 pounds. In some embodiments, the final compression force is about 3200 pounds to about 9600 pounds.

Equipment used in the methods of making the tablets may include, for example, a high speed mixing granulator, a fluid bed dryer, an extrusion granulator, a slugger press, or a roller compactor.

Methods of Using Tablets

By way of example but not limitation, the tablets described herein may be used to reduce or remove stains or decay from tooth enamel or dentin or used to clean root surfaces according to the following procedure.

A tablet may be inserted into an oral irrigator (such as ones produced by Water Pik, Fort Collins, Colo.) such that it is positioned in the fluid flow path of the irrigator. Examples of oral irrigators in which a tablet may be positioned in the fluid flow path include U.S. Provisional Patent Application No. 62/474,438, entitled "Oral Irrigator Handle For Use With Oral Hygiene Agent," filed Mar. 16, 2017; and U.S. Provisional Patent Application No. 62/516,227, entitled "Oral Irrigator Handle For Use With Oral Hygiene Agent," filed Jun. 7, 2017, which are incorporated herein by reference in their entireties.

When the irrigator is turned on, fluid, such as water, mouthwash, or an oral rinse, may flow through the irrigator and impinge the tablet. The tablet may disintegrate and release the abrasive. The dissolved tablet particles may be carried into a user's mouth by the fluid ejected from the tip of the oral irrigator. The abrasive-laden fluid may be directed at the teeth, and the impact of the abrasive may reduce or remove tooth decay or stains from enamel or dentin. The abrasive may also clean root surfaces. In general, the tablets may improve the oral cleaning efficiency of the irrigator.

As described in more detail in the Examples, the tablets may help clean teeth while causing no or minimal abrasion of the teeth surfaces. Use of the tablets in an oral irrigator may remove less of the tooth surface than a comparable amount of brushing.

In some embodiments, the tablets are water soluble and leave a clean or smooth feeling in the oral cavity. In some embodiments, the tablets are water soluble and do not leave a residual or gritty feeling in the oral cavity.

Methods of Using Abrasives

In some embodiments, an abrasive disclosed herein, such as glycine, is entrained in a stream of fluid, such as water. In the design and use of glycine in propelled fluid, the glycine may clean the surfaces of the teeth or roots.

In some embodiments, the fluid stream is pulsating. In one example, the stream pulsates at about 1200 pulses per minute. A pump or a valve may provide the pulsating action. For example, a pump may be driven by an electric motor and may comprise a small cylinder having a piston therein reciprocated by a Scotch-yoke drive. As another example, pressurized fluid flowing through an intermittent or oscillating valve may produce the pulsating stream of fluid.

The stream of fluid may be ejected directly from a water line or from a device such as an oral irrigator, a countertop-mounted irrigation device, or a hand-held irrigation device. The water line or device may be suitable for a professional setting or a home setting. In some embodiments, the device includes a nozzle with a cross-sectional area of about 0.035 and the nozzle aids in producing the pulses.

One example of a device for producing a stream of fluid in which glycine may be is carried is shown in FIG. 1.

A handle 100 of an oral irrigator is fluidly connected to a fluid source, such as a reservoir, by a connector 107 and a hose 108. The handle 100 is also fluidly connected to a removable tip 104, which may have a tip collar 106 that interfaces with the handle 100. Liquid from the fluid source can be expelled through a tip outlet 105 in the tip 104 when the tip 104 is connected to the handle 100. The tip 104 generally is configured to be inserted into a user's mouth and to expel fluid against a user's teeth, gums, tongue, etc.

A release button 110 positioned in or on the housing 102 can selectively release the tip 104 from the handle 100 or can provide access to an internal chamber in which presently disclosed tablet may be inserted. Examples of oral irrigator handles having an internal chamber include U.S. Provisional Patent Application No. 62/474,438, entitled "Oral Irrigator Handle For Use With Oral Hygiene Agent," filed Mar. 16, 2017; and U.S. Provisional Patent Application No. 62/516,227, entitled "Oral Irrigator Handle For Use With Oral Hygiene Agent," filed Jun. 7, 2017, which are incorporated herein by reference in their entireties.

In some embodiments, a pause actuator 112 positioned in or on the housing 102 selectively interrupts the flow of liquid from the fluid source to the tip 104.

In the handle 100 depicted in FIG. 1, the structure, such as a pump or valve, that produces the pulsating action of the fluid stream is positioned in a base unit (not shown). In some examples, the handle 100 is directly connected to a pressured water line and the pulse-producing structure is a valve located in the handle 100. In some examples, the handle 100 is a self-contained unit and the pulse-producing structure is located in the handle 100.

EXAMPLES

The following examples illustrate various aspects of the disclosure, and should not be considered limiting.

Example 1—Tablet Composition and Preparation

Tablets were prepared from the composition shown in Table 1. Weight percentages may be understood as relative proportions and do not sum to 100 percent due to variations in manufacturing protocols.

TABLE 1

| Component | Description | wt % |
|---|---|---|
| glycine | abrasive | 40 |
| Xylisorb ® 100 DC | filler | 40 |
| Aerosil ® 200 | glidant | 0.35 |
| Kollidon ® VA64 Fine | binder | 0-8 |
| Kollidon ® CL-F | disintegrant | 0-4 |
| magnesium stearate | lubricant | 1.5 |
| sodium lauryl sulfate | surfactant | 2 |
| sucralose | sweetener | 9 |
| peppermint spray dried | flavoring agent | 10 |

Xylisorb® 100 DC is granulated xylitol mixed with maize dextrin and was obtained from Roquette Pharma (Lestrem, France). Aerosil® 200 is amorphous anhydrous colloidal silicon dioxide and was obtained from Evonik Industries (Essen, Germany). Kollidon® VA64 Fine, a vinylpyrrolidone-vinyl acetate copolymers, and Kollidon® CL-F, a crospovidone, were obtained from BASF Corporation (Florham Park, N.J.). The glycine particles had an average particle size (Mv) of about 59 μm as measured by laser diffraction (Powdersize, Inc., Quakertown, Pa.).

The components in Table 1 were mixed dry with the magnesium stearate added last. The resulting powder mixtures had the physical properties presented in Table 2.

TABLE 2

| Physical Property | Value |
|---|---|
| Bulk Density | 0.707 g/cc |
| Tapped Density | 1.019 g/cc |
| Compressibility Index | 30.6 |
| Hausner Ratio | 1.44 |
| Loss on Drying | 0.7% |

The resulting powder mixture was placed directly into a tableting press with a long stroke and a pre-compression station. Tableting pressure was varied to control the hardness of the tablet and thereby the disintegration time and friability of the tablet. As one example, a mixture containing 2 wt % Kollidon® VA64 Fine was compressed with 2248 lbs of pre-compression force and 6400 lbs of final compression force to produce a tablet with a hardness of 7 kp (15.43 pounds).

Example 2A—Stain Removal by Tablet in Oral Irrigator

The effectiveness of the tablets of Example 1 to remove stains from teeth was tested by Salus Research, Inc. (Fort Wayne, Ind.) according to the following procedure.

Male and female adults between the ages of 18 and 65 who had at least 16 natural teeth including all 4 natural lower incisors in a good state of repair without extreme overlapping or overcrowding were recruited. At least 3 of the 4 incisors in each subject were free from full crowns or restorations. Each subject had mandibular anterior stain on the facial approximal and marginal areas of the tooth.

Before and after study participation, subjects' tooth stains were scored by an experienced dental examiner using the MacPherson modification of the Lobene Stain Index, which assesses both the intensity and area of stain present on the mesial and distal regions of each tooth. The facial surfaces of each incisor were divided into the following 4 segments: gingival or marginal (the 2 mm-wide strip running parallel to the gingival margin; the limit towards the incisal edge given by the end of the interdental papilla; body (the central area of buccal aspect between gingival and distal mesial sites, extending to the incisal edge), mesial score (the visible area between line angle and adjacent tooth, ending at the interdental papilla, i.e., the start of the gingival site), and the distal score (the visible area between line angle and adjacent tooth, ending at the interdental papilla, i.e., the start of the gingival site).

Each segment was scored for area of stain according to the following criteria: 0=no stain present, natural tooth color; 1=thin line of stain, may be discontinuous; 2=thick line or band of stain; and 3=stain covers entire area. Each segment was scored for intensity of stain according to the following criteria: 0=no stain; 1=faint stain, can be seen with close examination; 2=moderate stain, clearly visible and aesthetically unacceptable; and 3=heavy, dark stain, obvious and aesthetically unacceptable. The total proximal stain score for each subject was calculated by multiplying the individual area and intensity scores and averaging them.

Before and after study participation, subjects' oral soft tissue health was assessed by visual inspection of the oral cavity by a dental examiner using a dental light and mirror. Examined structures included the gingivae, hard and soft palate, oropharynx, buccal and labial mucosa, tongue, floor of the mouth, and lips. The site, size, and severity of any lesions and tentative diagnosis, if possible, were recorded. Following the study, an examiner also assessed whether any aberrations were attributable to treatment.

Subjects did not use any other dental device or oral care product during the course of the study.

Test tablets were placed in prototype tips that were inserted into oral irrigators (Water Pik, Fort Collins, Colo.). Subjects used the oral irrigators according to manufacturer's instructions for one minute each time for up to 5 times. The test tablets were dissolved in water ejected from the oral irrigator into the subjects' mouths and onto at least the mandibular anterior facial surfaces.

Following oral irrigation, a dental examiner re-assessed stain area, stain intensity and oral soft tissue health. Stain data is presented in Table 3 as mean scores for extrinsic stain using the modified Lobene Stain Index. The first data row presents averaged results for the 4 subjects who completed at least 3 minutes of treatment. The second data row presents averaged results for the 2 subjects that completed 5 minutes of treatment.

No damage to soft tissue was reported or observed.

TABLE 3

| | | | Modified Lobene Stain Index | | | | | |
|---|---|---|---|---|---|---|---|---|
| N | Age | Gender | Baseline Mean | 1 Min Mean | 2 Min Mean | 3 Min Mean | 4 Min Mean | 5 Min Mean |
| 4 | 34 | 4F | 1.83 | — | 1.33 | 1.16 | — | — |
| 2 | 26 | 2F | 1.91 | — | 1.38 | 1.19 | 0.88 | 0.66 |

Results demonstrate that the tablets of Example 1, when dissolved in water ejected from an oral irrigator into a subject's mouth, are safe on teeth and soft tissue.

Results demonstrate that extrinsic tooth stain was reduced by about 27% after 2 total minutes of tablet/oral irrigator use, by about 37% after 3 total minutes, by about 54% after 4 total minutes, and by about 64% after 5 total minutes.

Glycine is a water soluble amino acid and was expected to completely dissolve in the water ejected from an oral irrigator. Any teeth cleaning benefit of glycine or its particles was not expected to remain after entrainment of glycine in the fluid stream.

Example 2B—Stain Removal by Tablet in Oral Irrigator

The effectiveness of the tablets of Example 1 to remove stains from teeth was tested as described in Example 2A with the following changes.

Fifteen subjects were randomly assigned to 3 study groups: tablet with oral irrigator, oral irrigator alone, and brushing with a standard toothbrush (Oral B Indicator 35). Subjects performed their assigned oral hygiene protocol daily for 2 weeks.

Stain data is presented in Table 4 as mean scores for extrinsic stain using the modified Lobene Stain Index.

No damage to soft tissue was reported or observed.

TABLE 4

| | | | | Modified Lobene Stain Index | |
|---|---|---|---|---|---|
| Treatment | N | Age | Gender | Baseline | 2-Week |
| Tablet | 5 | 50 | 3 M, 2 F | 2.76 | 2.06 |
| Irrigator | 5 | 39 | 2 M, 3 F | 2.29 | 1.50 |
| Brushing | 5 | 45 | 1 M, 4 F | 2.36 | 2.40 |

Results demonstrate that the tablets of Example 1, when dissolved in water ejected from an oral irrigator into a subject's mouth, are safe on teeth and soft tissue.

Results demonstrate that the tablets of Example 1 reduced total stain after daily use for 2 weeks more so than brushing with a standard toothbrush.

Glycine is a water soluble amino acid and was expected to completely dissolve in the water ejected from an oral irrigator. Any teeth cleaning benefit of glycine or its particles was not expected to remain after entrainment of glycine in the fluid stream.

Example 3—Abrasion of Dentin

The effect of the tablets of Example 1 on dentin was studied by Dental Product Testing (Noblesville, Ind.) according to the following procedure.

Erupted or un-erupted human permanent teeth, free of carries, having at least a 3 mm×5 mm surface of preparable dentin were selected. Soft tissue was removed by scraping and the teeth were sterilized with sodium hypochlorite for at least 24 hours and then stored in a suitable medium (e.g., sterile 0.9% saline). Teeth were sectioned at the amelocemental junction with a dental burr or disc and the radicular portion was used for dentin specimens.

Specimens were mounted in cubic molds (10 mm×10 mm×10 mm) sized to fit the test apparatuses. The molds were constructed of a flexible material such as that used for dental impressions. The molds were filled with methyl methacrylate and the specimens were placed on top as flat as possible. The methacrylate was then allowed to cure.

Once cured, the surface of the block with the dentin exposed was serially ground and polished on silicon carbide disks. All 6 sides of the specimen blocks were ground with 320 grit wet $Al_2O_3$ paper on a lapidary wheel. The face having the specimen was ground just until the dentin was exposed. The specimen surface was then polished with 600 and 800 grit wet $Al_2O_3$ until well polished. Specimens were further polished by hand with 3 µm and 1 µm diamond slurry until the Ra (surface roughness) was less than 0.1 µm as determined by profilometry.

Specimens were made planoparallel by measuring side-to-side across the cube, in each dimension, using microcalipers. If the four measurements differed by more than 100 µm, hand polishing was repeated until satisfactory results were obtained.

Once planoparallel, the specimens were placed on a profilometer (Mitutoyo Surftest SV-2000 (Aurora, Ill.) or similar instrument with sensitivity to <0.1 µm) and five traces uniformly distributed across the surface were taken. The Ra of the specimen was less than 0.1 µm and the difference between the highest and lowest point did not exceed 10 µm. In addition, there were no concave or wavy contours.

Once smoothness and planoparallelness was established, the specimen was placed on a hardness microtester and four readings on the very edges of the specimen were taken to determine the Vicker Hardness Number (VHN) of the specimen. Dentin ranged between 30 VHN and 70 VHN.

Specimens were kept hydrated at all times during the preparation, abrasion, and measurement procedures.

Eight specimens were selected for each group. For the control (toothbrush) group, two pieces of PVC or polyester adhesive tape were placed parallel to each other on each specimen to expose a window of dentin approximately 3-4 mm wide. Such taping left 0.5-1 mm on each side of the 5 mm specimen to use as reference points. For the test groups, an additional two strips of tape placed perpendicular to the first strips left an approximately 2 mm×2 mm window of dentin. The small exposed surface made it easier to place an oral irrigator tip in the same area after removing the tip to reload an abrasive tablet in the irrigator.

Eight ISO toothbrushes (described in ISO 11609, Annex A: A.3.4: Toothbrushes) were selected and immersed in DI Water for 24 hours. Brushers were mounted on a V8 cross brushing machine (described in ISO 11609, Annex A: A.3.2.1). The brushes were preconditioned by brushing any substrate (not exclusively a dental substrate) for 20,000 strokes while the substrate was held in the specimen holder with 150 g tension.

Following brush preconditioning, the eight prepared dentin specimens for the control group were mounted on the brushing machine. The brush heads were aligned above the specimens such that the center row of bristles was centered on the specimen. The arm to which the brush was attached was moved to its highest point and the brush head was set so the front row of bristles came off the specimen at the shortest point in the reciprocal motion.

For the test group, a reference diluent, 0.5% CMC (carboxymethylcellulose-based artificial saliva) in 10% glycerin solution, was prepared (described in ISO 11609, Annex A: A.3.5). A reference abrasive slurry was prepared by admixing 10 g calcium pyrophosphate in 50 ml of 0.5% reference diluent (described in ISO 11609, Annex A: A.3.1 & A.3.6).

The reference slurry was mixed well to ensure uniform suspension and then applied to the heads of the brushing machine. Toothbrush force was 1.5 N (150 g) and total brush time was 5000 double strokes. After treatment, adhesive was removed from the specimens with 70% ethanol and the specimens were cleaned. The brushing machine was also cleaned well between runs to prevent carryover.

Surface profile measurements were collected no longer than 15 minutes after removing a specimen from water.

For the test groups, an oral irrigator (Water Pik, Fort Collins, Colo.) was used instead of a toothbrush.

Specimens were held on top of a scissor lift in clay to provide stability to the specimens. The specimens were positioned above the clay so no spray from the irrigator was trapped over them. The entire set-up was placed in the bottom of a deep sink to catch overspray. Distance between the irrigator and specimen was maintained by clamping an oral irrigator tip in a ring stand and measuring the distance between the tip and dentin with a feeler gauge (2 mm).

Tablets were prepared according to Example 1 and one tablet was inserted into the oral irrigator such that it was positioned in the flow path of the irrigator. The irrigator reservoir was filled with water. The irrigator was set to maximum power and to floss mode. The tip was positioned over the exposed dentin window. The oral irrigator ran for one programmed cycle (30 seconds on, brief pause, 18 seconds on). Profilometery data was collected (as described below) after the 48-second treatment, which simulated 6 months of usage (also as described below). Then the tape was reapplied and the specimen returned to its study position. A fresh tablet was inserted in the irrigator and the reservoir was filled with fresh water. The tip was returned to the same position over the exposed window and treatment was repeated for a total of 7 minutes and 12 second (7×1-min (30 seconds on, brief pause, 30 seconds on)+12 seconds), which simulated 5 years of usage. Adhesive was removed from the specimens and they were rinsed well with water and placed in a humid environment until analyzed.

Profilometry data was collected from the treated (taped) area of each specimen. Surface measurements were taken from just inside the previously taped zone across the exposed window and just into the opposite previously taped zone. The profilometry software calculated a mean from at least 100 z values across the scan. Five scans from different points along the exposed zone were taken and the mean of the five readings was calculated. The mean depth of the five traces per specimen was determined. Then the average depth of abrasion was determined for each group from the eight individual specimen values within the group.

Comparability of brushing and oral irrigator treatments was determined as follows. An oral irrigator tip traces a distance along the gums of 228 mm per arch, counting both inner and outer surfaces, with a spray 1 mm in diameter. The total treated area is therefore 456 $mm^2$. Considering a treatment time of 60 seconds, the resulting exposure is 0.132 $s/mm^2$. Two treatments per day for 365 days per year=96 seconds per year on any given $mm^2$.

An average brushing time is 1 minute, or 30 seconds per arch, or 15 seconds per quadrant. Each mouth quadrant has 5 surfaces (lingual of molars, occlusal of molars, buccal of molars, lingual of incisors, and buccal of incisors). At 15 seconds brushing per quadrant, each surface receives about 3 seconds of brushing. Brushing speed is about 5 strokes per second. Due to brush head length, the middle teeth of any given surface may receive 15 strokes. Twice daily brushing× 15 strokes per tooth×365 days per year=10950 strokes per tooth per year.

A standard brushing test uses 5000 strokes, which corresponds to approximately 6 months of brushing (i.e., ½ of 10950 strokes per tooth per year). For the oral irrigator, 48 seconds corresponds to about 6 months of use (i.e., ½ of 96 seconds per year on any given mm²). Accordingly, oral irrigator data was collected after 48 seconds of use, corresponding to 6 months of brushing, and after 8 minutes of use, corresponding to 5 years of twice daily brushing.

Results are presented in Table 5.

TABLE 5

| Treatment | Mean Depth of Dentin Abraded ± SEM (μm) |
|---|---|
| Tablet in oral irrigator, 48 seconds | 0.19 ± 0.02 |
| Tablet in oral irrigator, 8 minutes | 0.77 ± 0.06 |
| Brushing with toothbrush (5000 strokes) | 14.71 ± 2.97 |

The results of Table 5 demonstrate that brushing with a regular toothbrush abrades a noticeably greater amount of dentin than does applying a fluid stream laden with the dissolved tablets of Example 1. Brushing for a simulated 6 months (5000 strokes) caused a significantly (p<0.001) greater dentin material loss than oral irrigator use with a tablet for a simulated 6 months (48 seconds). Brushing for a simulated 6 months caused a significantly (p<0.001) greater dentin material loss than oral irrigator use with a tablet for a simulated 5 years (8 minutes).

Comparison by a student t-test of the two tablet groups reveals a significant (p<0.001) difference. The difference suggests a dose response from the tablet treatment.

Relative Dentine Abrasivity (RDA) values were calculated from the profilometry measurements and are presented in Table 6. The reference dentifrice is considered to have an RDA value of 100 in standard brushing models. Deviations from the standard model (i.e., use of an oral irrigator) can affect calculations and comparisons of RDA values.

TABLE 6

| Treatment | RDA |
|---|---|
| Tablet in oral irrigator, 48 seconds | 1.3 |
| Tablet in oral irrigator, 8 minutes | 5.2 |
| Brushing with toothbrush (5000 strokes) | 100.0 |

The data in Table 6 demonstrate that oral irrigator use with the disclosed tablets has much lower abrasivity values than standard brushing.

Example 4—Effect of Tablet Distance from Tip

The efficacy of tablet performance as a function of distance from the terminus of an oral irrigator tip (i.e., nozzle) was investigated. One study compared water ejected from a nozzle (FIG. 2A) with water ejected from a nozzle after contacting a tablet of Example 1 at about 3.5 inches (FIG. 2B), about 5 inches (FIG. 2C), or about 30 inches (FIG. 2D) from the nozzle terminus. For each treatment, the water pressure and the distance between the water outlet and a test stain were the same. Results are presented in FIGS. 2A-2D.

The tablets of Example 1 (FIGS. 2B-2D) were more effective at removing stains from teeth than water alone (FIG. 2A) regardless of the distance between the tablet and nozzle. Tablets of Example 1 were approximately equally effective at removing stains from teeth when the distance between the tablet and nozzle terminus was about 3.5 inches (FIG. 2B) to about 5 inches (FIG. 2C). When the distance between the tablet and nozzle terminus was increased to about 30 inches (FIG. 2D), the stain removal efficacy decreased compared to shorter distances (FIGS. 2B and 2C).

Results demonstrate that glycine of a given particle size is effective at a given distance from the nozzle and efficacy decreased as distance from the nozzle increased. If fluid flow rate remains constant, as the distance between a tablet and a nozzle increases, the time of exposure between tablet particles (such as glycine) and fluid increases. Increased exposure may decrease entrained particle size such that the user does not feel residual hard particles in the mouth or on surrounding surfaces (such as the face or a bathroom counter).

Although various embodiments have been described above with a certain degree of particularity, or with reference to one or more individual embodiments, those skilled in the art could make numerous alterations to the disclosed embodiments without departing from the spirit or scope of this disclosure. Other embodiments are therefore contemplated. All matter contained in the above description is illustrative only of particular embodiments and is not limiting. Changes in detail or structure can be made without departing from the basic elements described herein.

What is claimed is:

1. An oral hygiene tablet comprising:
   an abrasive consisting of glycine wherein the glycine has an average (Mv) particle size of 50 μm to 90 μm, and the glycine does not include a surface coating,
   a bulking agent comprising xylitol and maize dextrin,
   a glidant comprising fumed silica, the fumed silica having an average particle size of 0.06 to 0.18 μm, and
   one or more of a binder, a disintegrant, a lubricant, a surfactant, a sweetener, and a flavoring agent.

2. The tablet of claim 1, wherein 35% by weight or less of the glycine particles have a particle size below 45 μm.

3. The tablet of claim 1, wherein 35% by weight or less of the glycine particles have a particle size greater than 100 μm.

4. The tablet of claim 1, wherein the glycine is present at 32 wt % to 48 wt %.

5. The tablet of claim 1, wherein the bulking agent is present at 32 wt % to 48 wt %.

6. The tablet of claim 1, wherein the average particle size of the fumed silica is about 0.12 μm.

7. The tablet of claim 1, wherein the tablet includes a disintegrant and the disintegrant is crospovidone.

8. The tablet of claim 1, wherein the tablet includes a lubricant and the lubricant is magnesium stearate.

9. The tablet of claim 1, wherein the tablet includes a surfactant and the surfactant is sodium lauryl sulfate.

10. The tablet of claim 1, wherein the tablet includes a sweetener and the sweetener is sucralose.

11. A method for cleaning teeth, the method comprising:
   providing a tablet, the tablet comprising
      a water-soluble abrasive having an average (Mv) particle size of 50 μm to 90 μm, wherein the water-soluble abrasive does not include a surface coating, and
      one or more of a binder, bulking agent, a disintegrant, a glidant, a lubricant, a surfactant, a sweetener, and a flavoring agent; and
   eroding the tablet with a liquid stream to produce a suspension of particles in the liquid,
   wherein the particles are transported to the tooth by the liquid stream, and the particles clean the teeth.

12. The method of claim 11, wherein the abrasive is an amino acid.

13. The method of claim 12, wherein the amino acid is glycine.

14. A method of reducing a stain on a tooth comprising:
providing a tablet comprising
   glycine,
   xylitol, and
   one or more of a binder, a lubricant, a disintegrant, a glidant, a surfactant, a sweetener, and a flavoring agent; and
eroding the tablet with a pulsating liquid stream to produce a suspension of particles in the liquid,
wherein the particles are transported to the tooth by the liquid stream, and the particles reduce the stain on the tooth.

15. The method of claim 14, wherein the glycine abrades the stain from the tooth.

16. The method of claim 14, wherein the stain shows an average 27% improvement in a modified Lobene Stain Index after 2 minutes of application of the particle-laden liquid.

17. The method of claim 14, wherein the stain shows an average 64% improvement in a modified Lobene Stain Index after 5 minutes of application of the particle-laden liquid.

18. The method of claim 14, wherein less dentin is abraded by the method than by brushing with a toothbrush for 10 times the amount of time.

19. The method of claim 14, wherein less than 0.2 µm of dentin is abraded after 48 seconds of application of the particle-laden liquid.

20. The method of claim 11, wherein the liquid stream is a pulsating liquid stream.

21. The method of claim 14, wherein the liquid stream pulsates at about 1200 pulses per minute.

* * * * *